United States Patent
Rule et al.

(10) Patent No.: US 9,594,070 B2
(45) Date of Patent: Mar. 14, 2017

(54) METHOD USING HALOGENATED BENZOIC ACID ESTERS AND ALDEHYDES FOR HYDRAULIC FRACTURING AND FOR TRACING PETROLEUM PRODUCTION

(71) Applicant: Spectrum Tracer Services, LLC, Tulsa, OK (US)

(72) Inventors: Jeffrey David Rule, Claremore, OK (US); Steve Allen Faurot, Skiatook, OK (US)

(73) Assignee: SPECTRUM TRACER SERVICES, LLC, Tulsa, OK (US)

( * ) Notice: Subject to any disclaimer, the term of this patent is extended or adjusted under 35 U.S.C. 154(b) by 545 days.

(21) Appl. No.: 14/072,556

(22) Filed: Nov. 5, 2013

(65) Prior Publication Data

US 2015/0323515 A1    Nov. 12, 2015

(51) Int. Cl.
*G01N 33/24* (2006.01)
*E21B 43/26* (2006.01)
*E21B 43/267* (2006.01)
*E21B 47/10* (2012.01)
*C09K 8/03* (2006.01)
*C09K 8/62* (2006.01)
*C09K 8/92* (2006.01)

(52) U.S. Cl.
CPC ............ *G01N 33/241* (2013.01); *C09K 8/03* (2013.01); *C09K 8/62* (2013.01); *C09K 8/92* (2013.01); *E21B 43/26* (2013.01); *E21B 43/267* (2013.01); *E21B 47/1015* (2013.01)

(58) Field of Classification Search
CPC ...................................................... G01N 33/24
USPC .................... 436/25, 27–29, 56, 128–129
See application file for complete search history.

(56) References Cited

U.S. PATENT DOCUMENTS

| | | | | |
|---|---|---|---|---|
| 3,342,263 | A | * | 9/1967 | Fischer ................... C09K 8/92 166/283 |
| 3,891,413 | A | * | 6/1975 | Sievers .................... G21F 9/12 210/656 |
| 3,902,362 | A | | 9/1975 | Tomisch et al. |
| 3,936,458 | A | * | 2/1976 | Sturm ................. C07D 215/08 504/247 |
| 3,993,131 | A | | 11/1976 | Riedel |
| 4,090,398 | A | | 5/1978 | Deans et al. |
| 4,168,746 | A | * | 9/1979 | Sheely .................... C09K 8/58 166/252.2 |
| 4,211,662 | A | * | 7/1980 | King .................... C10M 161/00 508/141 |
| 4,223,725 | A | | 9/1980 | Teasdale et al. |
| 4,231,426 | A | | 11/1980 | Carter et al. |
| 4,303,411 | A | | 12/1981 | Chen et al. |
| 4,420,565 | A | | 12/1983 | Schmitt |
| 4,439,344 | A | * | 3/1984 | Albanese ............... A01N 25/24 106/10 |
| 4,520,109 | A | | 5/1985 | Simmonds et al. |
| 4,555,489 | A | | 11/1985 | Schmitt |
| 4,690,689 | A | | 9/1987 | Malcosky et al. |
| 4,722,394 | A | | 2/1988 | Wellington et al. |
| 4,725,551 | A | | 2/1988 | Thompson |
| 4,742,873 | A | | 5/1988 | Craig, III |
| 4,783,314 | A | | 11/1988 | Hoots et al. |
| 4,826,689 | A | * | 5/1989 | Violanto .................. A61K 9/14 210/639 |
| 4,960,884 | A | * | 10/1990 | Roush .................... A01N 31/04 514/717 |
| 5,114,676 | A | | 5/1992 | Leiner et al. |
| 5,128,358 | A | * | 7/1992 | Saccomano ........... C07C 217/60 514/392 |
| 5,212,093 | A | | 5/1993 | Richardson et al. |
| 5,246,860 | A | * | 9/1993 | Hutchins ............... G01N 33/241 116/250 |
| 5,649,596 | A | | 7/1997 | Jones et al. |
| 5,798,319 | A | * | 8/1998 | Schlosberg ............. C07C 69/44 507/100 |
| 5,905,036 | A | * | 5/1999 | Pope ......................... B09C 1/00 166/250.01 |
| 6,003,365 | A | * | 12/1999 | Pope ......................... B09C 1/00 166/246 |
| 6,192,985 | B1 | | 2/2001 | Hinkel et al. |
| 6,321,595 | B1 | * | 11/2001 | Pope ......................... B09C 1/00 166/252.2 |
| 6,326,398 | B1 | * | 12/2001 | Chiang ................. C07C 235/74 514/535 |
| 6,331,436 | B1 | | 12/2001 | Richardson et al. |
| 6,645,769 | B2 | | 11/2003 | Tayebi et al. |

(Continued)

FOREIGN PATENT DOCUMENTS

| | | | |
|---|---|---|---|
| DE | 4424712 | * | 1/1996 |
| EP | 0282232 A2 | | 9/1988 |
| JP | 04-139299 | * | 5/1992 |

OTHER PUBLICATIONS

Bowman, R. S. et al, Ground Water 1992, 30, 8-14.*
Serres-Piole, C. et al, Journal of Chromatography A 2011, 1218, 5872-5877.*
Steinberg, S. M. et al, Water Research 1995, 29, 965-969.*
Spectrum Tracer Services LLC Home webpage, 4 pages, downloaded Nov. 21, 2016 from http://www.spectrumtracer.com/.*
Anthony Crasto Reagents webpage on the Jonesd Reagent, 4 pages, downloaded Nov. 21, 2016 from https://sites.google.com/site/anthonycrastoreagents/jones-reagent.*
EOG Resources Inc amemded Hydraulic Fracturing Fluid Disclosure, submitted Feb. 2, 2015, downloaded Nov. 21, 2016 from http://ocdimage.emnrd.state.nm.us/imaging/filestore/SantaFe/WF/20150311/30025420860000_03_11_2015_09_33_16.pdf.*

(Continued)

*Primary Examiner* — Arlen Soderquist
(74) *Attorney, Agent, or Firm* — Dennis D. Brown; Brown Patent Law, P.L.L.C.

(57) ABSTRACT

A method of hydraulic fracturing, and tracer composites for use in the fracturing procedure, for tracing the production of crude oil or other hydrocarbon liquid products from one or more fractured zones. The tracer composites preferably include an oil soluble tracer adsorbed onto a solid carrier material. A non-water soluble coating is preferable also included on the composite over the tracer compound.

15 Claims, No Drawings

(56) References Cited

U.S. PATENT DOCUMENTS

| | | | |
|---|---|---|---|
| 6,659,175 B2 | 12/2003 | Malone et al. | |
| 6,725,926 B2 | 4/2004 | Nguyen et al. | |
| 7,032,622 B2 | 4/2006 | Kitamura et al. | |
| 7,032,662 B2* | 4/2006 | Malone | E21B 47/1015 166/250.1 |
| 7,347,260 B2* | 3/2008 | Ferguson | E21B 47/1015 166/250.12 |
| 7,410,011 B2* | 8/2008 | Anderson | E21B 47/1015 166/250.12 |
| 7,472,748 B2 | 1/2009 | Gdanski et al. | |
| 7,491,682 B2 | 2/2009 | Gupta et al. | |
| 7,493,955 B2 | 2/2009 | Gupta et al. | |
| 8,393,395 B2 | 3/2013 | Cochet et al. | |
| 8,445,480 B2* | 5/2013 | Hunt | C07D 413/10 514/211.15 |
| 8,640,773 B2 | 2/2014 | Hewitt et al. | |
| 2002/0049191 A1* | 4/2002 | Springer | C07D 501/00 514/203 |
| 2003/0006036 A1* | 1/2003 | Malone | E21B 47/1015 166/250.12 |
| 2004/0094297 A1* | 5/2004 | Malone | E21B 47/1015 166/250.12 |
| 2004/0110302 A1* | 6/2004 | Vamvakaris | C10L 1/003 436/56 |
| 2004/0142922 A1* | 7/2004 | Alanine | C07D 317/46 514/217.03 |
| 2004/0192728 A1* | 9/2004 | Codd | C07D 215/38 514/313 |
| 2006/0052251 A1* | 3/2006 | Anderson | E21B 47/1015 507/103 |
| 2006/0124301 A1 | 6/2006 | Gupta et al. | |
| 2006/0144588 A1* | 7/2006 | Ferguson | E21B 47/1015 166/252.6 |
| 2006/0165622 A1* | 7/2006 | Hiramoto | A61K 8/347 424/65 |
| 2007/0148356 A1* | 6/2007 | Russell | C09D 5/008 427/384 |
| 2007/0215385 A1* | 9/2007 | Anderson | E21B 47/1015 175/42 |
| 2008/0011776 A1 | 1/2008 | Patel et al. | |
| 2010/0307745 A1 | 12/2010 | Lafitte et al. | |
| 2011/0220360 A1 | 9/2011 | Lindvig et al. | |
| 2011/0257887 A1 | 10/2011 | Cooper et al. | |
| 2011/0260051 A1* | 10/2011 | Preudhomme | E21B 43/16 250/282 |
| 2011/0277996 A1* | 11/2011 | Cullick | E21B 33/138 166/250.12 |
| 2012/0289716 A1 | 11/2012 | Suzuki et al. | |
| 2013/0031971 A1 | 2/2013 | Freese et al. | |
| 2013/0084643 A1* | 4/2013 | Commarieu | C09K 8/03 436/27 |
| 2014/0294675 A1* | 10/2014 | Melker | A61B 5/082 422/84 |
| 2015/0005315 A1* | 1/2015 | Carroll | C07D 295/13 514/253.12 |
| 2015/0110722 A1* | 4/2015 | Hohn | A61K 49/0457 424/9.44 |

OTHER PUBLICATIONS

PCT/US2014/063707; International Search Report and Written Opinion; Feb. 12, 2015; Applicant: Spectrum Tracer Services, LLC; Published in: WO.

National Institute of Standards and Technology. Methyl 4-Flourobenzoate; Material Measurement Laboratory; Jan. 2, 2011; Internet: www.webbook.nist.gov/cgi/cbook.cgi?ID+403-33-8&Units=SI.

Gilley, et al., Adsorption of Bromide Tracers onto Sediment, Biological Systems Engineering, Jan. 1, 1990.

Greenkorn, Experimental Study of Waterflood Tracers, Journal of Petroleum Technology, Jan. 1962, pp. 87-92.

Bowman, Evaluation of Some New Tracers for Soil Water Studies, Soil Science Soc. Am. J., vol. 48, 1984, pp. 987-993.

SPE 31094, Pope, et al., Field Study of Guar Removal from Hydraulic Fractures, Society of Petroleum Engineers, 1996.

SPE 35233, McLaughlin, et al., Radioactive Tracers: Review of Principle Factors in Design and Application, Society of Petroleum Engineers, 1996.

SPE 39920, Willberg, et al., Optimization of Fracture Cleanup Using Flowback Analysis, Society of Petroleum Engineers, 1998.

SPE 56427, Dugstad, et al., Application of Tracers to Monitor Fluid Flow in the Snorre Field: A Field Study, Society of Petroleum Engineers, 1999.

Davis, et al., An Introduction to Ground-Water Tracers, National Technical Information Service, Mar. 1985.

* cited by examiner

METHOD USING HALOGENATED BENZOIC ACID ESTERS AND ALDEHYDES FOR HYDRAULIC FRACTURING AND FOR TRACING PETROLEUM PRODUCTION

FIELD OF THE INVENTION

The present invention relates to methods of hydraulic fracturing and to tracer composites which can be used in conjunction with hydraulic fracturing procedures to trace the production of crude oil or other liquid hydrocarbon materials from individual or multiple fractured zones.

BACKGROUND OF THE INVENTION

When conducting a hydraulic fracturing operation, a hydraulic fracturing fluid is pumped into a subterranean formation under sufficient pressure to create, expand, and/or extend fractures in the formation and to thus provide enhanced recovery of the formation fluid. Hydraulic fracturing fluids typically comprise water and sand, or other proppant materials, and also commonly include various types of chemical additives. Examples of such additives include: gelling agents which assist in suspending the proppant material; crosslinkers which help to maintain fluid viscosity at increased temperatures; gel breakers which operate to break the gel suspension after the fracture is formed and the proppant is in place; friction reducers; clay inhibitors; corrosion inhibitors; scale inhibitors; acids; surfactants; antimicrobial agents; and others.

Fracturing operations have long been conducted in both low permeability and high permeability formations in order, for example, to increase the rate of production of hydrocarbon products or to increase the injection rates of water or gas injection wells. Moreover, with the introduction of slickwater fracturing procedures which use large quantities of water containing friction reducers, it is now also possible to stimulate naturally fractured shales by fracturing multiple intervals during staged treatments in horizontal wellbores. Treatment of all zones of interest in a horizontal well may require several hours to a few days to complete.

Heretofore, when conducting hydraulic fracturing operations in vertical wells, well logging, microseismic, or other techniques have been used to determine production rates and/or the position, length, and height of each fracture. However, when, for example, a horizontal well extending through a shale formation is fractured in multiple stages, microseismic analysis is essentially unable to determine which of the fractured stages are successfully producing oil and/or gas products and which are not. Moreover, the impeller apparatuses used in production logging tools do not function satisfactorily in horizontal wells. Therefore, neither technique is able to reliably determine (a) whether production is occurring from any given stage, (b) the amount of production from any given stage, or (c) the comparative amounts of production from multiple stages.

Consequently, a need has long existed for a method for reliably (a) confirming that crude oil or other liquid hydrocarbon products are being produced from specific fractured zones, (b) determining the rate of liquid hydrocarbon production from a fractured formation zone, or (c) determining the comparative rates of liquid hydrocarbon production from multiple fractured zones, particularly in horizontal wells. Such information would be of great benefit to the operator in (1) identifying possible actions or repairs which would provide immediate improvement, (2) selecting and optimizing enhanced recovery procedures, (3) optimizing the operation of an enhanced lifting system used in the well, (4) reducing water production and the lifting costs associated therewith, and (5) optimizing the performance and cost effectiveness of fracturing and other completion procedures used in other wells drilled in the same field.

Water soluble chemical tracers have been used heretofore in hydraulic fracturing operations to trace the return of the aqueous fracturing fluid. These water soluble tracers are intended to dissolve in and flow with the aqueous fracturing fluid. Thus, they are only able to provide an indication of (a) how much of the fracturing fluid is recovered from, or undesirably remains in, the formation and (b) the comparative recovery of the fracturing fluid, or lack thereof, from one fractured zone versus another.

Consequently, water soluble tracers used for tracing the return or loss of the injected fracturing fluids are not capable of determining whether any hydrocarbon product is actually being produced from a particular zone of a multi-zone well or how much hydrocarbon product is being produced from one zone versus another.

In addition, attempts made heretofore by those in the art to develop and use oil soluble tracers to trace oil production from fractured zones have not been satisfactory. One approach attempted heretofore has been to deliver viscous tracer emulsions into fractured zones. However, such emulsions can be broken, for example, by (1) the heat within the formation, (2) the pumping and formation pressures to which the emulsions are subjected, (3) the shear forces exerted on the emulsions during pumping and injection, and (4) exposure to water flow within the subterranean formation. In addition, such emulsions commonly have a low specific gravity such that the emulsions can separate and accumulate in higher regions of the fractured zone. Consequently, when attempting to evaluate the tracer analysis, the operator cannot be confident that a significant amount of the tracer emulsion (a) was not pushed or washed out of the fractured zone, (b) did not drift and accumulate in higher pockets, or (c) was even properly received in the fractured zone in the first place.

SUMMARY OF THE INVENTION

The present invention satisfies the needs and alleviates the problems discussed above. In one aspect, there is provided a tracer composite for use in tracing the production of crude oil or other liquid hydrocarbon products. The tracer composite preferably comprises: (a) a solid carrier material which is substantially non-soluble in water and (b) a tracer carried on the carrier material, wherein the tracer is preferably a halogenated benzoic ester, a halogenated benzoic aldehyde, or a halogenated benzoic acid.

In another aspect, there is provided a tracer composite for use in tracing the production of crude oil or other liquid hydrocarbon products wherein the composite preferably comprises: (a) a solid carrier material, (b) an oil soluble tracer carried on the carrier material, and (c) a coating on the tracer composite over the tracer, the coating being formed of a petroleum based grease.

In another aspect, there is provided a method of producing a tracer composite for use in tracing the production of crude oil or other liquid hydrocarbon products, the method preferably comprising the steps of: (a) adsorbing a tracer on a solid carrier material to form a composite base, wherein the carrier material is substantially non-soluble in water and the tracer is a halogenated benzoic ester, a halogenated benzoic aldehyde, or a halogenated benzoic acid, and then (b) applying a coating to the composite base, wherein the coating is formed of a grease material which is substantially non-soluble in water. In this method, step (b) preferably comprises adding a solvent to the grease material to form a solution and spraying misting the solution onto the composite base. The solution is preferably sprayed misted onto the composite base while the composite base is tumbled, agitated, flowed, whirled, or a combination thereof.

In another aspect, there is provided a method of fracturing, and tracing production from, a subterranean formation, the method preferably comprising the steps of: (a) injecting a fracturing fluid into a fracturing zone of the subterranean formation wherein: at least a portion of the fracturing fluid includes an amount of a tracer composite material, the tracer composite material comprises a tracer on a solid carrier material, the carrier material is substantially non-soluble in water, and the tracer is a halogenated benzoic ester, a halogenated benzoic aldehyde, or a halogenated benzoic acid, and (b) analyzing a product recovered from a well associated with the subterranean formation for a presence of the tracer to determine whether the product includes crude oil or other liquid hydrocarbon material produced from the fracturing zone.

In another aspect of the fracturing method just described, the fracturing zone which is fractured in step (a) is a first fracturing zone and the method preferably further comprises the steps of: (c) injecting, prior to step (b), a fracturing fluid into a second fracturing zone of the subterranean formation wherein: at least a portion of the fracturing fluid injected into the second fracturing zone includes an amount of a second tracer composite material, the second tracer composite material comprises a second tracer on a solid carrier material, the carrier material of the second tracer composite material is substantially non-soluble in water, the second tracer is different from said first tracer, and the second tracer is a halogenated benzoic ester, a halogenated benzoic aldehyde, or a halogenated benzoic acid, and (d) analyzing the product recovered from the well for a presence of the second tracer to determine whether the product includes crude oil or other liquid hydrocarbon material produced from the second fracturing zone.

Further aspects, features, and advantages of the present invention will be apparent to those of ordinary skill in the art upon reading the following Detailed Description of the Preferred Embodiments.

DETAILED DESCRIPTION OF THE PREFERRED EMBODIMENTS

The present invention provides (1) a method of hydraulic fracturing, (2) tracer composites which can be used in various types of downhole operations and are particularly well suited for use in the inventive fracturing method, and (3) a method for forming the inventive tracer composites.

The inventive fracturing method and tracer composites can be used in single stage or multistage fracturing operations and are particularly well suited for use in multistage hydraulic fracturing operations such as those conducted in horizontal wells. Using the inventive hydraulic fracturing method and tracer composites, the well operator can determine: (a) whether crude oil or other hydrocarbon liquid products are being produced from any given fractured zone; (b) how much liquid hydrocarbon product is being produced from the fractured zone; and (c) the comparative liquid hydrocarbon recovery from each fractured zone versus the other fractured zones in the well.

The inventive tracer composite comprises: (1) a solid carrier material which is preferably non-soluble or substantially non-soluble in water and (2) an oil soluble tracer which is preferably adsorbed on the solid carrier material. The inventive tracer composite will preferably also include a coating which is formed on the tracer composite over the tracer. The coating will preferably be miscible in oil but non-soluble or substantially non-soluble in water.

As used herein and in the claims, the term "oil soluble tracer" means that the tracer is sufficiently soluble in oil so that, when the tracer is contacted by crude oil or other liquid hydrocarbon products, the liquid hydrocarbon products will move the tracer out of the inventive tracer composite in a detectable amount.

The oil soluble tracer used in forming the inventive composite can generally be any type of traceable material which is preferably: (a) soluble in crude oil; (b) chemically stable under the temperature, pressure and other physical conditions to which the tracer will be exposed within the subterranean formation; (c) substantially chemically inert with respect to the other components of the fracturing fluid and to the liquids, solids, and gases within the formation; and (d) analytically detectable at low concentration levels (most preferably in parts per billion).

Examples of oil soluble tracers preferred for use in the inventive composite include, but are not limited to, halogenated benzoic esters, halogenated benzoic aldehydes, and halogenated benzoic acids. The oil soluble tracers used in the inventive composites will more preferably be halogenated benzoic esters or halogenated benzoic aldehydes which are non-soluble or substantially non-soluble in water and will most preferably be halogenated benzoic esters.

The more preferred use of a tracer compound which is non-soluble or substantially non-soluble in water (i.e., a tracer having hydrophobic properties) assists in preventing the tracer compound from being prematurely leached out of the fractured zone due to the interaction of the tracer composite with the aqueous fracturing fluid or with water present in the subterranean formation. The leaching out of the tracer compound can result in the loss of the tracer material and can also produce false positive readings for the fractured zone in the oil production analysis.

As used herein and in the claims, the term "substantially non-soluble in water" means that the solubility of the particular carrier material, coating, or tracer compound being described is not more than 1 gram per liter of water at 25° C. and 100 kPa.

Halogenated benzoic acid tracers used in the inventive composites will preferably be compounds of the formula:

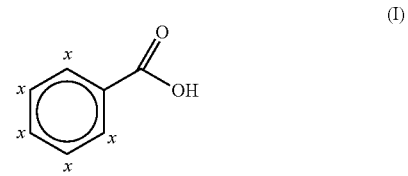

(I)

Wherein at least one x in the formula is a chlorine, fluorine, or bromine atom and each remaining x is chlorine, fluorine, bromine, or hydrogen.

Halogenated benzoic aldehydes used in the inventive composites will preferably be compounds of the formula:

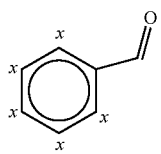

(II)

Wherein at least one x in the formula is a chlorine, fluorine, or bromine atom and each remaining x is chlorine, fluorine, bromine, or hydrogen.

The halogenated benzoic esters used in the inventive composites will preferably be compounds formed by the reaction of halogenated benzoic acids with alcohols. Such esters will therefore preferably be compounds of the formula:

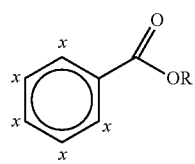

(III)

wherein
each x in the formula is a chlorine, fluorine, bromine, or hydrogen atom,
at least one x in the formula is a chlorine, fluorine, or bromine atom, and
R is a straight chained, branched chained, or aromatic hydrocarbon constituent group (more preferably an alkane, alkene, alkyne, arene) having from 1 to 10 carbon atoms.

The type and length of the alcohol compound (R—OH) used in forming the halogenated benzoic ester of formula III will typically affect the physical properties of the ester such that, as the size and complexity of the hydrocarbon constituent group R increases, the melting and boiling points of the ester will generally increase and the ester will generally become more hydrophobic. However, as the size of the R constituent group increases (i.e., as the ester becomes more waxy in nature), the maximum molar amount of the ester which can be adsorbed onto the composite carrier will generally also be reduced.

Due to their effectiveness, desirable physical properties, availability, lower cost, and ease of production, one group of halogenated benzoic esters that are preferred for use as tracers in the inventive composite are halogenated benzoic esters having the formula III shown above which are produce by reacting halogenated benzoic acids (preferably fluorobenzoic acids) with methanol so that the R constituent of the resulting ester is a methyl group. Examples of such methyl esters include, but are not limited to: methyl 2,4-difluorobenzoate; methyl 2,3,4,5-tetrafluorobenzoate; methyl 3,4,5-trifluorobenzoate; methyl 2,4,5-trifluorobenzoate; methyl 3,5-difluorobenzoate; methyl 2,6-difluorobenzoate; methyl 2-fluorobenzoate; methyl 4-fluorobenzoate; methyl 3,4-difluorobenzoate; methyl pentafluorobenzoate; methyl 2,5-difluorobenzoate; methyl 3-fluorobenzoate; and methyl 2,3-difluorobenzoate. Due to their availability and cost, particularly preferred oil soluble tracers within this group are methyl 2-fluorobenzoate, methyl 3-fluorobenzoate, and methyl 4-fluorobenzoate.

As noted above, the solid carrier material used in forming the inventive tracer composite will preferably be non-soluble or substantially non-soluble in water. In addition, all or substantially all (i.e., at least 95% by weight) of the solid carrier material will preferably be within a particle size range of from 6 to 200 mesh and will more preferably be within a particle size range of from 10 to 48 mesh. The carrier material will also preferably have a pore size in the range of from about 20 to about 150 Å, a porosity of from about 10 to about 50%, and a specific gravity of greater than 1.0. The porous carrier particles will most preferably be capable of adsorbing an amount of the tracer of up to 50% by weight of the carrier material.

The carrier material will preferably be formed of charcoal. The carrier will most preferably be formed of charcoal which has been activated by heating (e.g., at about 150° C. for about 12 hours, preferably under vacuum) to desorb water therefrom.

Examples of other suitable carrier materials include, but are not limited to, diatomaceous earth, ceramic, expanded clay, silica gel, aeroclay, aerogel, or expanded glass. Prior to loading the oil soluble tracer thereon, each of these carrier materials will also preferably be heated (e.g., at about 150° C. for about 12 hours, preferably under vacuum) to desorb water therefrom.

Further, when using silica gel, ceramic, aeroclay, aerogel, or expanded glass, in order to deactivate hydrophilic groups on the surfaces of the porous material, the material will also preferably be silanized by contacting with a silanizing agent such as hexamethyldisilazane, chlorotrimethylsilane, or poly-(dimethylsiloxane). The silanizing agent will preferably be applied in the form of a solvent solution (e.g., an acetonitrile or hexane solution) and the treated carrier material will preferably be drained and dried prior to applying the tracer thereto.

The activation, silanizing, and/or other pre-treatment of the carrier material to cause the carrier material to be more hydrophobic further prevents the oil soluble tracer from being prematurely leached out of the fractured zone due to interaction with the aqueous fracturing fluid or formation water.

Following the activation and/or other pre-treatment of the solid carrier material, the oil soluble tracer is preferable adsorbed onto the carrier by combining the tracer with a solvent and adding the solution to the carrier, preferably under vacuum conditions and at an elevated temperature (e.g., in a vacuum dryer) in order to evaporate the solvent and leave the oil soluble tracer on the external surfaces and the internal pore surfaces of the carrier material. Examples of suitable solvents include, but are not limited to, methanol, hexane, dichloromethane, isopropyl alcohol, and acetone. Preferred application and drying conditions will typically be about 300 millibar and 50° C.

The amount of tracer compound adsorbed onto the solid carrier material will preferably be from about 5% to about 40% by weight of the weight of the carrier material. The amount of adsorbed tracer compound will more preferably be from about 10% to about 30% and will most preferably be from about 10% to about 20% by weight of the weight of the solid carrier material.

Although the inventive tracer composite has thus far been described as having only one tracer compound adsorbed onto the solid carrier material, it will be understood that two or more tracer compounds can alternatively be simultaneously or sequentially adsorbed onto the carrier of the inventive composite using the inventive method.

As noted above, the inventive tracer composite also preferably includes a coating which is applied to the composite over the tracer compound. The coating will preferably be non-soluble or substantially non-soluble in water and will further prevent the oil soluble tracer from being prematurely leached out of the fractured zone due to interaction with the aqueous fracturing fluid or formation water. The application of the coating to the inventive composite is particularly preferred and beneficial when the tracer adsorbed onto the carrier material is a halogenated benzoic acid or other material which is soluble or somewhat soluble in water.

Examples of materials suitable for forming coatings for the inventive tracer composites include, but are not limited to, grease, wax, fluoropolymers, or similar materials which are non-soluble or substantially non-soluble in water. The coating will preferably be formed of petroleum based grease and will most preferably be formed of lithium grease.

The amount of coating material applied to the inventive tracer composite will preferably be in the range of from about 0.05% to about 0.5% by weight of the total weight of the coated composite and will preferably be of a thickness in the range of from about 0.005 to about 0.1 millimeters. Most preferably, the amount of coating material will be about 0.1% by weight of the total weight of the coated composite and the thickness of the coating material will be about 0.01 mm.

By way of example, but not by way of limitation, a grease, wax, or similar coating can be applied to the inventive composite over the adsorbed tracer compound by: (a) dissolving (while warming if necessary) the coating material in a sufficient amount of a strong, quick evaporating solvent such as dichloromethane to allow the coating material to be applied in the form of a spray mist and then (b) applying the coating solution to the composite by spray mist while tumbling, agitating, flowing, and/or whirling the composite in, e.g., a cement-type mixer, a rotoclone dryer, or other apparatus.

In accordance with the inventive method for fracturing a subterranean formation, an aqueous hydraulic fracturing fluid is injected into a formation zone under pressure. The hydraulic fracturing fluid will typically include a proppant material (i.e., a solid material which is different from the tracer composite provided by the present invention) and can generally also include any number of other fracturing fluid components of the type described above or otherwise used in the art. In addition, in the inventive method, an amount of an inventive tracer composite is also added to all or a portion of the injected fracturing fluid so that the inventive tracer composite is placed and remains in the formation fracture along with the proppant material.

The inventive tracer composite can be added to the fracturing fluid in the blender tub used for forming the proppant slurry. Alternatively, the tracer composite can be combined with water and a sufficient amount of a thickener (e.g., from about 9 to about 10 parts by weight xanthan gum per hundred parts by weight of water) to form an aqueous slurry of the tracer composite which can be injected into the fracturing fluid as the fracturing fluid is being pumped into the well.

In order to optimize the placement and use of the tracer composite in the fracture, the tracer composite will preferably not be included in any pad or pre pad portion of the fracturing fluid injected into the fracturing zone at the beginning of the fracturing procedure or in any flush portion of the fracturing fluid injected at the end of the fracturing procedure. As will be understood by those in the art, the initial pad or pre pad portion of the fracturing fluid typically does not include any proppant material and is used to initiate the fracture. Also, if the pad injection pressure either does not reach fracturing pressure (i.e., the fluid is simply flowing freely into the formation) or the pad is blocked-in and is unable to initiate a fracture in the attempted injection zone, then the fracturing procedure for the stage in question will be discontinued. The flush portion of the fracturing fluid also typically does not include any proppant material and is used to push the last of the proppant into the formation fracture.

Most preferably, when employed either in fracturing procedures which use proppant materials or in other types of fracturing procedures (e.g., acid fracturing) which do not use proppant materials, the inventive tracer composite will be added to all or most of the middle 90%, 85%, 80%, 75%, 70%, 65%, 60%, 55%, 50%, 45%, or 40% portion of the total fracturing fluid injected into the formation zone. In addition, the amount of the inventive tracer composite material added to the fracturing fluid will preferably be in the range of from about 0.1 to about 5 kilograms, more preferably from about 1 to about 2 kilograms, of the inventive composite material per fractured zone.

In a horizontal or other well having multiple fracturing stages, the inventive fracturing procedure described above using the inventive tracer composite can be performed in one, a plurality, or all of the multiple fracturing zones. However, the inventive tracer composites added to the fracturing fluids used to fracture the different formation zones will include different oil soluble tracers of the type describe above so that (a) the presence of one or more tracers in the crude oil or other hydrocarbon liquid product produced from the well will indicated the particular fractured zone or zones from which the product was derived and (b) the concentrations of the tracers in the liquid hydrocarbon product, or in the liquid hydrocarbon portion/layer of a combined oil and water product, can be used to determine the amount of liquid hydrocarbon product being produced from any given zone, or the comparative hydrocarbon liquid recovery from one zone versus the others.

The product stream from the well can be sampled as frequently as desired, or continuously analyzed, to determine the presence of any of the oil soluble tracers from the various fractured zones in the hydrocarbon product fluid. By way of example, but not by way of limitation, the presence and concentration of each unique oil soluble tracer of formula I, II, or III illustrated above in an oil product sample or in the oil layer of a product sample can be determined by directly analyzing the oil using a gas or liquid chromatograph with a mass spectrographic detector, or using other standard laboratory techniques. However, when analyzing the oil product directly, care must be taken to ensure that the organic components present in the crude oil matrix do not contaminate the instrument or otherwise interfere with the sample analysis.

Alternatively, as an example of a more preferred procedure where one, a plurality, or all of the oil soluble tracers used in the various fractured zones are halogenated benzoic esters having the molecular structure III illustrated above, an aqueous NaOH solution can be added to the oil layer of the product sample to hydrate any halogenated benzoic esters present in the oil and thereby produce corresponding halogenated benzoate and alcohol products which will separate from the oil in an aqueous phase. The aqueous phase can then be separated from the oil and analyzed, without interference from the organic components of the oil, for the presence and concentration of each unique halogenated benzoate using, for example, a liquid chromatograph with a mass spectrographic detector, or using other standard laboratory techniques.

Similarly, if one, a plurality, or all of the oil soluble tracers used in the various fractured zones are halogenated benzoic aldehydes having the molecular structure II illustrated above, Jones reagent or other strong oxidizing agent can be added to the oil layer of the product sample to react with any halogenated benzoic aldehydes present in the oil and thereby produce corresponding halogenated benzoate products which will separate from the oil into an aqueous phase. The aqueous phase can then be separated from the oil and analyzed, without interference from the organic components of the oil, for the presence and concentration of each unique halogenated benzoate using, for example, a liquid chromatograph with a mass spectrographic detector, or using other standard laboratory techniques.

On the other hand, if one, a plurality, or all of the oil soluble tracers used in the various fractured zones are halogenated benzoic acids having the molecular structure I illustrated above, then at the pH levels typically encountered, the halogenated benzoates of these acids will automatically move to the aqueous layer of the sample. However, if the sample does not have an aqueous layer, the halogenated benzoic acid tracer(s) can be recovered from the hydrocarbon sample, and detected using the same procedures mention above, by adding an amount of water to the sample having a pH of greater than 7.

It will also be understood that, although the well from which the hydrocarbon production samples are taken for tracer analysis will typically be the same well through which the hydraulic fracturing fluids were delivered into the formation, samples for tracer analysis can also or alternatively be taken from one or more other wells which are also associated with the fractured formation.

The following example is meant to illustrate, but in no way limit, the claimed invention.

EXAMPLE

Twenty grams of carbon having a particle size of 8-20 mesh were activated by baking at 250° C. for 6 hours.

200 microliters of methyl 4-fluorobenzoate were mixed with 15 ml of methanol to form an oil soluble tracer (OST) solution. The OST solution was added to a 40 ml vial containing 10 g of the activated carbon and the vial was place in a Rapivap apparatus at 300 mBar and 60° C. for 2 hours to form a dried OST on carbon composite.

0.01 grams of lithium grease and 5 ml of methylene chloride were placed in a 20 ml vial and mixed until homogenized. The mixture was then poured into the 40 ml vial containing the dried OST/carbon composite and the vial was shaken until all of the composite material was wet. Next, the 40 ml vial was placed in the Rapivap apparatus at 300 mBar and 50° C. for 1 hour to form a coated OST composite.

The OST composite was then mixed with 1 kg of sand to form a proppant/OST mixture. The mixture was transferred into a 6 ml syringe. Next, a sufficient amount of oil was added to saturate the mixture and then 3 ml of oil was delivered through the sample and recovered for analysis.

This same procedure was then repeated except that water rather than oil was delivered through the proppant/OST mixture.

The analyses of the resulting oil and water products showed that a significant amount of the methyl 4-fluorobenzoate tracer which would be sufficiently detectable for field usage was released when the proppant/OST mixture was eluted with oil. However, only a trace amount which would not be of significance in field usage was released when the proppant/OST mixture was eluted with water.

Thus, the present invention is well adapted to carry out the objectives and attain the ends and advantages mentioned above as well as those inherent therein. While presently preferred embodiments have been described for purposes of this disclosure, numerous changes and modifications will be apparent to those of ordinary skill in the art. Such changes and modifications are encompassed within this invention as defined by the claims.

What is claimed:

1. A method of fracturing and tracing crude oil production from a subterranean formation, said method comprising the steps of:
    (a) injecting an aqueous fracturing fluid into a fracturing zone of a subterranean formation wherein: at least a portion of said aqueous fracturing fluid includes an amount of a tracer composite material, said tracer composite material comprises a tracer on a solid carrier material, said carrier material is substantially non-soluble in water, said carrier material is activated charcoal, said aqueous fracturing fluid comprises water and a proppant material, said tracer composite material is different from said proppant material, said tracer is oil soluble, said tracer is substantially inert with respect to said aqueous fracturing fluid, said tracer is chemically stable under all conditions in said subterranean formation so that said tracer does not substantially react with other substances or form other products in said subterranean formation, and said tracer is a halogenated benzoic ester having a formula

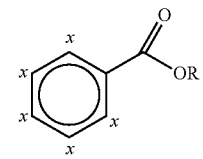

wherein
each x in said formula is a chlorine, fluorine, bromine, or hydrogen atom,
at least one x in said formula is a chlorine, fluorine, or bromine atom, and
R is a straight chained, branched chained, or aromatic hydrocarbon constituent group having from 1 to 10 carbon atoms, and
    (b) analyzing a crude oil product or a crude oil phase of a product recovered from a well associated with said subterranean formation for a presence of said tracer in said crude oil product or said crude oil phase of said product to determine whether said crude oil product or said crude oil phase of said product includes crude oil produced from said fracturing zone,
wherein step (b) comprises (i) adding a NaOH solution to said crude oil product or said crude oil phase of said product recovered from said well to hydrate said tracer to produce a halogenated benzoate which separates from said crude oil product or said crude oil phase of said product into an aqueous phase and then (ii) analyzing said aqueous phase for said halogenated benzoate.

2. The method of claim 1 wherein R is a methyl group.

3. The method of claim 1 wherein said tracer is methyl 2-fluorobenzoate, methyl 3-fluorobenzoate, or methyl 4-fluorobenzoate.

4. The method of claim 1 further comprising the step, prior to step (a), of injecting an initial pad material into said fracturing zone, wherein said tracer composite material is not included in said initial pad material.

5. The method of claim 1 further comprising the step, after step (a), of injecting a final flush material into said fracturing zone, wherein said tracer composite material is not included in said final flush material.

6. The method of claim 1 wherein said fracturing zone is a first fracturing zone, said tracer composite material is a first tracer composite material, said tracer is a first tracer, and said method further comprises the steps of:
(c) injecting, prior to step (b), an aqueous fracturing fluid into a second fracturing zone of said subterranean formation wherein: at least a portion of said aqueous fracturing fluid injected into said second fracturing zone includes an amount of a second tracer composite material, said second tracer composite material comprises a second tracer on a solid carrier material, said carrier material of said second tracer composite material is substantially non-soluble in water, said carrier material of said second tracer composite material is activated charcoal, said aqueous fracturing fluid injected into said second fracturing zone comprises water and a proppant material, said second tracer is oil soluble, said second tracer is substantially inert with respect to said aqueous fracturing fluid injected into said second fracturing zone, said second tracer is chemically stable under all conditions in said subterranean formation so that said second tracer does not substantially react with other substances or form other products in said subterranean formation, said second tracer is different from said first tracer, and said second tracer is a halogenated benzoic aldehyde or said second tracer is a halogenated benzoic ester having a formula

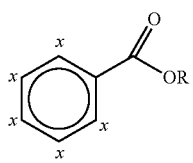

wherein
each x in said formula is a chlorine, fluorine, bromine, or hydrogen atom,
at least one x in said formula is a chlorine, fluorine, or bromine atom, and
R is a straight chained, branched chained, or aromatic hydrocarbon constituent group having from 1 to 10 carbon atoms, and
(d) analyzing said crude oil product or said crude oil phase of said product recovered from said well for a presence of said second tracer in said crude oil product or said crude oil phase of said product to determine whether said crude oil product or said crude oil phase of said product includes crude oil produced from said second fracturing zone.

7. The method of claim 6 wherein each of said first tracer and said second tracer is a halogenated benzoic ester having a formula

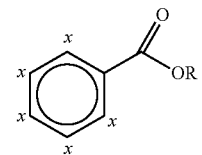

wherein
each x in said formula is a chlorine, fluorine, bromine, or hydrogen atom,
at least one x in said formula is a chlorine, fluorine, or bromine atom, and
R is a straight chained, branched chained, or aromatic hydrocarbon constituent group having from 1 to 10 carbon atoms.

8. The method of claim 6 further comprising the steps of:
prior to step (a), injecting an initial pad material into said first fracturing zone, wherein said first tracer composite material is not included in said initial pad material injected into said first fracturing zone and
prior to step (c), injecting an initial pad material into said second fracturing zone, wherein said second tracer composite material is not included in said initial pad material injected into said second fracturing zone.

9. The method of claim 6 further comprising the steps of:
after step (a), injecting a final flush material into said first fracturing zone, wherein said first tracer composite material is not included in said final flush material injected into said first fracturing zone and
after step (c), injecting a final flush material into said second fracturing zone, wherein said second tracer composite material is not included in said final flush material injected into said second fracturing zone.

10. The method of claim 1 wherein said carrier material has a pore size in a range of from 20 to 150 Å.

11. A method of fracturing and tracing crude oil production from a subterranean formation, said method comprising the steps of:
(a) injecting a first aqueous fracturing fluid into a first fracturing zone of a subterranean formation wherein: at least a portion of said first aqueous fracturing fluid includes an amount of a first tracer composite material, said first tracer composite material comprises a first tracer on a solid activated charcoal carrier material which is substantially non-soluble in water, said first aqueous fracturing fluid comprises water and a proppant material, and said first tracer is an oil soluble halogenated benzoic ester which (i) is substantially inert with respect to said first aqueous fracturing fluid and (ii) is chemically stable under all conditions in said subterranean formation so that said first tracer does not substantially react with other substances or form other products in said subterranean formation;
(b) injecting a second aqueous fracturing fluid into a second fracturing zone of said subterranean formation wherein: at least a portion of said second aqueous fracturing fluid includes an amount of a second tracer composite material, said second tracer composite material comprises a second tracer on a solid activated charcoal carrier material which is substantially non-soluble in water, said second aqueous fracturing fluid comprises water and a proppant material, and said second tracer is an oil soluble halogenated benzoic ester which (i) is substantially inert with respect to said second aqueous fracturing fluid, (ii) is chemically stable under all conditions in said subterranean formation so that said second tracer does not substantially react with other substances or form other products in said subterranean formation, and (iii) is different from said first tracer, wherein each of said first tracer and said second tracer is an oil soluble halogenated benzoic ester having a formula

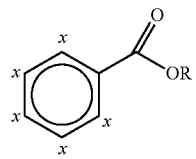

wherein each x in said formula is a chlorine, fluorine, bromine, or hydrogen atom, at least one x in said formula is a chlorine, fluorine, or bromine atom, and R is a methyl constituent group, and (c) analyzing a crude oil product or a crude oil phase of a product recovered from a well associated with said subterranean formation for a presence of said first tracer and said second tracer in said crude oil product or said crude oil phase of said product to determine whether said crude oil product or said crude oil phase of said product includes crude oil produced from said first fracturing zone, said second fracturing zone, or both said first fracturing zone and said second fracturing zone, wherein step (c) comprises (i) adding a NaOH solution to said crude oil product or said crude oil phase of said product recovered from said well to hydrate said first and said second tracers to produce halogenated benzoates which separate from said crude oil product or said crude oil phase of said product into an aqueous phase and (ii) then analyzing said aqueous phase for said halogenated benzoates.

12. A method of fracturing and tracing crude oil production from a subterranean formation, said method comprising the steps of:
(a) injecting an aqueous fracturing fluid into a fracturing zone of a subterranean formation wherein: at least a portion of said aqueous fracturing fluid includes an amount of a tracer composite material, said tracer composite material comprises a tracer on a solid carrier material, said carrier material is substantially non-soluble in water, said carrier material is activated charcoal, said aqueous fracturing fluid comprises water and a proppant material, said tracer composite material is different from said proppant material, said tracer is oil soluble, said tracer is substantially inert with respect to said aqueous fracturing fluid, said tracer is chemically stable under all conditions in said subterranean formation so that said tracer does not substantially react with other substances or form other products in said subterranean formation, and said tracer is a halogenated benzoic aldehyde and
(b) analyzing a crude oil product or a crude oil phase of a product recovered from a well associated with said subterranean formation for a presence of said tracer in said crude oil product or said crude oil phase of said product to determine whether said crude oil product or said crude oil phase of said product includes crude oil produced from said fracturing zone.

13. The method of claim 12 wherein step (b) comprises (i) adding Jones reagent to said crude oil or said crude oil phase of said product recovered from said well to react with said tracer to produce a halogenated benzoate which separates from said crude oil or said crude oil phase of said product into an aqueous phase and then (ii) analyzing said aqueous phase for said halogenated benzoate.

14. The method of claim 12 wherein said fracturing zone is a first fracturing zone, said tracer composite material is a first tracer composite material, said tracer is a first tracer, and said method further comprises the steps of:
(c) injecting, prior to step (b), an aqueous fracturing fluid into a second fracturing zone of said subterranean formation wherein: at least a portion of said aqueous fracturing fluid injected into said second fracturing zone includes an amount of a second tracer composite material, said second tracer composite material comprises a second tracer on a solid carrier material, said carrier material of said second tracer composite material is substantially non-soluble in water, said carrier material of said second tracer composite material is activated charcoal, said aqueous fracturing fluid injected into said second fracturing zone comprises water and a proppant material, said second tracer is oil soluble, said second tracer is substantially inert with respect to said aqueous fracturing fluid injected into said second fracturing zone, said second tracer is chemically stable under all conditions in said subterranean formation so that said second tracer does not substantially react with other substances or form other products in said subterranean formation, said second tracer is different from said first tracer, and said second tracer is a halogenated benzoic aldehyde and
(d) analyzing said crude oil product or said crude oil phase of said product recovered from said well for a presence of said second tracer in said crude oil product or said crude oil phase of said product to determine whether said crude oil product or said crude oil phase of said product includes crude oil produced from said second fracturing zone.

15. A method of fracturing and tracing crude oil production from a subterranean formation, said method comprising the steps of:
(a) injecting an aqueous fracturing fluid into a fracturing zone of a subterranean formation wherein: at least a portion of said aqueous fracturing fluid includes an amount of a tracer composite material, said tracer composite material comprises a tracer on a solid carrier material, said carrier material is substantially non-soluble in water, said carrier material is activated charcoal, said aqueous fracturing fluid comprises water and a proppant material, said tracer composite material is different from said proppant material, said tracer is oil soluble, said tracer is substantially inert with respect to said aqueous fracturing fluid, said tracer is chemically stable under all conditions in said subterranean formation so that said tracer does not substantially react with other substances or form other products in said subterranean formation, and said tracer is a halogenated benzoic ester having a formula

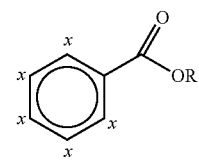

wherein
- each x in said formula is a chlorine, fluorine, bromine, or hydrogen atom,
- at least one x in said formula is a chlorine, fluorine, or bromine atom, and
- R is a straight chained, branched chained, or aromatic hydrocarbon constituent group having from 1 to 10 carbon atoms, and (b) analyzing a crude oil product or a crude oil phase of a product recovered from a well associated with said subterranean formation for a presence of said tracer in said crude oil product or said crude oil phase of said product to determine whether said crude oil product or said crude oil phase of said product includes crude oil produced from said fracturing zone, wherein step (b) comprises (i) hydrating said tracer in said crude oil product or said crude oil phase of said product to produce a halogenated benzoate which separates from said crude oil product or said crude oil phase of said product into an aqueous phase and then (ii) analyzing said aqueous phase for said halogenated benzoate.

* * * * *